US012011248B2

(12) United States Patent
Miyaoka et al.

(10) Patent No.: US 12,011,248 B2
(45) Date of Patent: Jun. 18, 2024

(54) MULTI-DETECTOR PERSONALIZED HOME DOSIMETRY GARMENT

(71) Applicant: University of Washington, Seattle, WA (US)

(72) Inventors: Robert S. Miyaoka, Seattle, WA (US); Hubert Vesselle, Seattle, WA (US); Robert Stewart, Seattle, WA (US); Robert L. Harrison, Seattle, WA (US); Larry A. Pierce, II, Seattle, WA (US)

(73) Assignee: University of Washington, Seattle, WA (US)

( * ) Notice: Subject to any disclaimer, the term of this patent is extended or adjusted under 35 U.S.C. 154(b) by 898 days.

(21) Appl. No.: 17/045,112

(22) PCT Filed: May 10, 2019

(86) PCT No.: PCT/US2019/031880
§ 371 (c)(1),
(2) Date: Oct. 2, 2020

(87) PCT Pub. No.: WO2019/217928
PCT Pub. Date: Nov. 14, 2019

(65) Prior Publication Data
US 2021/0228078 A1 Jul. 29, 2021

Related U.S. Application Data

(60) Provisional application No. 62/669,884, filed on May 10, 2018.

(51) Int. Cl.
*A61B 5/00* (2006.01)
*A61B 5/06* (2006.01)
(Continued)

(52) U.S. Cl.
CPC .......... *A61B 5/0024* (2013.01); *A61B 5/0022* (2013.01); *A61B 5/0033* (2013.01);
(Continued)

(58) Field of Classification Search
CPC ... A61B 6/5235; A61B 5/6804; A61B 5/6805; A61B 6/4266; A61B 5/0024;
(Continued)

(56) References Cited

U.S. PATENT DOCUMENTS 6,194,725 B1   2/2001   Colsher et al.
6,205,347 B1   3/2001   Morgan et al.
(Continued)

FOREIGN PATENT DOCUMENTS

CA         2941409 A1     9/2014
CN         105813570 A    7/2016
(Continued)

OTHER PUBLICATIONS

"A Multi-Detector Personalized Home Dosimetry (MD PHD) Vest for @Home Monitoring of Lu-177 DOTATATE Peptide Receptor Radionuclide Therapy (PRRT)," IEEE 2018 NSS/MIC/RTSD Conference Presentation, 9 pages.
(Continued)

*Primary Examiner* — Colin T. Sakamoto
*Assistant Examiner* — Tommy T Ly
(74) *Attorney, Agent, or Firm* — CHRISTENSEN O'CONNOR JOHNSON KINDNESS PLLC (57) ABSTRACT

A garment for detecting radiation washout (e.g., radioactivity concentrations) in organs includes a covering that wraps around and is secured to the body. The covering permits positron emission tomography-computed tomography (PET/CT) imaging of the body through the covering. The garment includes guides formed from a material that is visible in a computed tomography (CT) image of the garment, such that
(Continued)

the guides are visible in CT images of user organs that the garment overlies. A plurality of radiation detectors are attached to the covering in a configuration customized for the body. A wiring system connects the plurality of radiation detectors to a power and data control system that is configured to transmit data from the garment to a remote service provider.

5 Claims, 4 Drawing Sheets

(51) Int. Cl.
  *A61B 6/42* (2024.01)
  *G01T 1/02* (2006.01)
  *G01T 1/29* (2006.01)

(52) U.S. Cl.
  CPC .......... *A61B 5/066* (2013.01); *A61B 5/6805* (2013.01); *A61B 6/4266* (2013.01); *G01T 1/02* (2013.01); *G01T 1/29* (2013.01)

(58) Field of Classification Search
  CPC ... A61B 5/0022; A61B 5/1001; A61B 5/1031; G01T 1/02; A61N 5/1027; A61N 5/103; A61N 5/1039; A61N 5/1071; A61N 5/1075
  See application file for complete search history.

(56) References Cited

U.S. PATENT DOCUMENTS

| | | |
|---|---|---|
| 6,381,482 B1 | 4/2002 | Jayaraman et al. |
| 7,291,841 B2 | 11/2007 | Nelson et al. |
| 8,260,013 B2 | 9/2012 | Pekar et al. |
| 8,705,831 B2 | 4/2014 | Koehler et al. |
| 9,002,438 B2 | 4/2015 | Knowland et al. |
| 9,029,791 B1 | 5/2015 | Kovalski et al. |
| 9,939,533 B2 | 4/2018 | Knowland et al. |
| 10,206,639 B2 | 2/2019 | Verma et al. |
| 10,653,374 B1 | 5/2020 | Thomas et al. |
| 10,852,446 B2 | 12/2020 | Knowland et al. |
| 2003/0193032 A1 | 10/2003 | Marshall |
| 2004/0008810 A1 | 1/2004 | Nelson et al. |
| 2004/0236207 A1 | 11/2004 | Widener et al. |
| 2009/0145655 A1 | 6/2009 | Gladd et al. |
| 2009/0154655 A1 | 6/2009 | Mackey |
| 2011/0112856 A1 | 5/2011 | Rousso et al. |
| 2011/0208044 A1 | 8/2011 | Edwards et al. |
| 2012/0150017 A1 | 6/2012 | Yamaya et al. |
| 2012/0165651 A1 | 6/2012 | Yamaya et al. |
| 2014/0088401 A1 | 3/2014 | Cai et al. |
| 2014/0100469 A1* | 4/2014 | Sagalovich ............. A61B 5/02 600/300 |
| 2014/0135593 A1 | 5/2014 | Jayalth et al. |
| 2014/0225926 A1 | 8/2014 | Mathers |
| 2014/0275939 A1 | 9/2014 | Mitteldorf |
| 2015/0301204 A1 | 10/2015 | Srivastava et al. |
| 2016/0103227 A1 | 4/2016 | Beddar et al. |
| 2017/0007177 A1 | 1/2017 | Valdastri et al. |
| 2017/0086763 A1 | 3/2017 | Verma et al. |
| 2017/0100493 A1 | 4/2017 | Sander et al. |
| 2017/0219720 A1 | 8/2017 | Cortesi et al. |
| 2021/0038920 A1 | 2/2021 | Gao et al. |
| 2021/0055432 A1 | 2/2021 | Rho |

FOREIGN PATENT DOCUMENTS

| | | |
|---|---|---|
| CN | 108378866 A | 8/2018 |
| DE | 102011083853 A1 | 4/2013 |
| DE | 102013212983 A1 | 1/2014 |
| EP | 2967465 A1 | 1/2016 |
| GB | 2405044 A | 2/2005 |
| JP | 6377574 B2 | 8/2018 |
| JP | 6434206 B2 | 12/2018 |
| WO | 2014/143222 A1 | 9/2014 |
| WO | 2017/115340 A1 | 7/2017 |
| WO | 2020/133400 A1 | 7/2020 |

OTHER PUBLICATIONS

Calais, P.J., and J.H. Turner, "Outpatient I-Rituximab Radioimmunotherapy for Non-Hodgkin Lymphoma," Clinical Nuclear Medicine 37(8):732-737, Aug. 2012.

Del Prete, M, et al., "Personalized Lu-octreotate peptide receptor radionuclide therapy of neuroendocrine tumours: a simulation study," Eur J Nucl Med Mol Imaging 44:1490-1500, 2017.

Fragogeorgi, E., et al., "Exploitation of SiPM technology for the development of a Theranostic Imaging device," The Journal of Nuclear Medicine 56(3):1-4, May 2015.

Levin, D.N., et al., "Retrospective Geometric Correlation of MR, CT, and PET Images," Radiology 169(3):817-823, Dec. 1988.

Li, Y., et al., "Fully-Depleted Silicon-on-Insulator Devices for Radiation Dosimetry in Cancer Therapy," IEEE Transactions on Nuclear Science 61(6):3443-3450, Dec. 2014.

Melroy, S., et al., "Development and Design of Next-Generation Head-Mounted Ambulatory Microdose Positron-Emission Tomography (AM-PET) System," Sensors 17(1164):1-15, 2017.

Mijnheer, B., et al., "In vivo dosimetry in external beam radiotherapy," American Association of Physicists in Medicine 40(7):070903-1-070903-19, Jul. 2013.

Nascimento, L.F., et al., "Application of Al2O3:C+ fibre dosimeters for 290 MeV/n carbon therapeutic beam dosimetry," Radiation Physics and Chemistry 115:75-80, 2015.

Nascimento, L.F., et al., "Medical dosimetry using a RL/OSL prototype," Radiation Measurements 71:359-363, 2014.

Osovizky, A., et al., "SENTIRAD—An innovative personal radiation detector based on a scintillation detector and a silicon photomultiplier," Nuclear Instruments and Methods in Physics Research A 652:41-44, 2011.

Park, H.M. and K.S. Joo, "Feasability of a wireless gamma probe in radioguided surgery," Physics in Medicine & Biology 61:N311-N321, 2016.

Perks, C.A., et al., "Medical dosimetry using Optically Stimulated Luminescence dots and microStar® readers," Landauer Europe, Oxford, United Kingdom; Landauer Europe, Cedex, France, Oct. 2018.

Proffitt, J., et al., "A Flexible High-Rate USB2 Data Acquisition System for PET and SPECT Imaging," 2005 IEEE Nuclear Science Symposium Conference Record, pp. 2971-2975.

Surti, S. and J.S. Karp, "Design considerations for a limited-angle, dedicated breast, TOF PET scanner," Physics in Medicine & Biology 53(11):2911-2921, Jun. 2008.

Turkington, T.G., et al., "PET Prostate Imaging with Small Planar Detectors," IEEE Conference Paper, Nov. 1, 2004, 5 pages.

Vandenberghe, S. and I. Lemahieu, "System characteristics of simulated limited angle TOF PET," Nuclear Instruments and Methods in Physics Research A 571:480-483, 2007.

Williams, G.V.M and S.G. Raymond, "Fiber-optic-coupled RbMgF3:Eu2+ for remote radiation dosimetry," Radiation Measurements 46:1099-1102, 2011.

Xie, Q., et al., "Conceptual Design and Simulation Study of an ROI-Focused Panel-PET Scanner," PLoS ONE 8(8):1-9, 2013.

Xu, H., et al., "Resolution modeling in projection space using a factorized multi-block detector response function for PET image reconstruction," Physics in Medicine & Biology 64, 2019, 17 pages.

Yamaya, T., et al., "A proposal of an open PET geometry," Physics in Medicine & Biology 53:757-773, 2008.

European Extended Search Report dated Jan. 31, 2022, issued in corresponding European Application No. 19799233.2, filed May 10, 2019, 9 pages.

International Search Report and Written Opinion dated Aug. 2, 2019, issued in corresponding International Application No. PCT/US2019/031880, filed May 10, 2019, 8 pages.

* cited by examiner

MULTI-DETECTOR PERSONALIZED HOME DOSIMETRY GARMENT

CROSS-REFERENCE TO RELATED APPLICATION

This application claims benefit to U.S. Provisional Patent Application No. 62/669,884, filed May 10, 2018, which is hereby incorporated by reference, in its entirety.

STATEMENT OF GOVERNMENT LICENSE RIGHTS

This invention was made with Government support under Contract No. R01CA042593 awarded by the National Institutes of Health The Government has certain rights in the invention.

BACKGROUND

Radiation therapy uses ionizing radiation to kill cancer cells and shrink tumors by damaging the cells' DNA. A common form of radiation therapy is external radiation therapy, wherein a limited area of the body is irradiated with a beam of x-rays to the main tumor. Unsealed source radiotherapy (also referred to as targeted radionuclide therapy, unsealed source radionuclide therapy, and molecular radiotherapy), on the other hand, is a systemic treatment using a radiopharmaceutical comprising a cell-targeting molecule combined or "labeled" with a radionuclide. The radiopharmaceutical is designed to deliver a toxic level of radiation to targeted disease sites. However, unlike tumor-directed drugs and toxins that kill only the directly targeted cells, radionuclides may destroy adjacent tumor cells even if they lack the specific tumor-associated antigen or receptor. A systemically administered targeted radiopharmaceutical may simultaneously eliminate both a primary tumor site and cancer that has spread throughout the body, including malignant cell populations undetectable by diagnostic imaging. In internal targeted radionuclide therapy the radiopharmaceutical is typically introduced into a subject by injection or ingestion. The cell-targeting molecule transports the radionuclide to a desired location, organ, or tissue, depending on the properties and administration of the radiopharmaceutical.

For example, peptide receptor radionuclide therapy (PRRT) is an unsealed source radiotherapy used for treating neuroendocrine tumors (NETs) wherein the radiopharmaceutical is a cell-targeting protein or peptide combined with a radionuclide. When injected into the bloodstream the radio-peptide travels to and binds to NET cells, delivering a targeted high dose of radiation directly to the cancer cells. Octreotide (DOTATOC) and octreotate (DOTATATE), for example, are laboratory-made versions of the hormone that binds to somatostatin receptors on NETs. In PRRT, the somatostatin analogue is combined with a therapeutic dose of the radionuclide. Yttrium-90 and Lutetium-177 are commonly used radionuclides.

For patients with metastatic, somatostatin-receptor-2 (SSTR2) NETs, targeted therapy using 177 Lu-DOTATATE has been found to greatly increase progression-free survival (PFS). Now that 177 Lu-DOTATATE has FDA approval it is quickly becoming the standard of care (SOC) for symptomatic NET patients and those with metastatic spread. FDA package instructions call for patients to receive a standardized regimen of four 7.4 GBq treatments, regardless of size, weight, gender, or patient health status. Under current SOC, in the United States the treatment is not personalized. However, studies show that personalized therapies can increase PFS and overall survival (OS) by over 100% if treatments continue until dosing to the kidneys reaches 23 Gy (i.e., the recommend kidney OAR cutoff). Practical tools are needed to accurately assess dose to the OARs, and in particular the kidney, which is the main OAR for 98% of NET patients receiving $^{177}$Lu-DOTATATE therapy. These tools will enable treatment personalization and improve outcomes beyond the proposed SOC protocol. In 2014, there were 171,000 NET patients with an estimated incidence rate of new cases of 6.98/100,000 per year (over 22,000 new patients). Eighty-one percent of NETs are SSTR2 positive, so a need exists for improved $^{177}$Lu-DOTATATE dosimetry. In addition, the teachings disclosed herein will be applicable to other promising theranostics protocols currently under development.

Medical research is striving towards individualized therapies and precision treatments. Standardized therapy is counter to the ideals of personalized medicine. For example, some patients may receive damaging levels of radiation to their kidneys (i.e., >23 Gy) if they receive the SOC four 7.4 GBq doses of $^{177}$Lu-DOTATATE. Knowing the actual dose to the kidneys is important because the kidneys are a main OAR in ~98% of patients. Other OARs include liver, spleen, and bone marrow. Without active monitoring, physicians will not know the dose to the kidneys or other OARs. In addition to avoiding potential harm to patients, and potentially more importantly, without dosimetry monitoring many patients will be underdosed. Recent studies indicate that patients who continued to receive $^{177}$Lu-DOTATATE treatments until their kidney dose reached 23 Gy (i.e., 3 to 9 treatments) had >100% increase in PFS (i.e., 33 vs. 15 months) and OS (i.e., 54 vs. 25 months) than patients whose treatments stopped before their kidneys received 23 Gy.

Although 177 Lu-DOTATATE organ dosimetry is common in Europe and elsewhere in the world, it is currently not common in the United States. We believe this is due to the high costs for repeated SPECT/CT imaging to perform personalized dosimetry, and the costs and inconvenience to patients and their families associated with requiring additional clinic visits for dose monitoring.

For example, a protocol for PRRT may require a series of four PRRT treatments with $^{177}$Lu-DOTATATE spaced approximately two months apart. The treatments may be performed as an outpatient procedure, or as an inpatient procedure requiring a hospital stay for several days. Each session typically starts with providing an anti-nausea medicine, followed by an amino acid solution delivered intravenously. The radionuclide is then injected, followed by additional amino acid solution.

For radionuclide theranostics, there is benefit to monitor the levels of radiation in patient organs (e.g., OARs) and in tumors in the patient's body, for days or weeks. Cancer cells overexpress the somatostatin receptor, which preferentially bind octreotide and target the radioactive compound directly at tumors. In addition to neuroendocrine tumors, PRRT and similar treatments using radioisotopes have been used to effectively treat bone metastases, thyroid cancers, and lymphomas.

One of the challenges associated with molecular radiotherapies is that patients can dramatically differ in their ability to absorb the radioactive molecules and/or in their ability to flush the radioactive molecules from their body. Knowing this, physicians may personalize treatments by monitoring absorbed radiation dosage at both the tumor site and at OARs. Unfortunately, repeated imaging of radionuclides is costly and time consuming for patients. There exists a great need to lessen the monitoring and treatment-adjusting burden on both patients and physicians, while also improve quality of care, and quality of life.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A garment for detecting organ radioactivity concentrations in organs of a body undergoing a targeted radionuclide therapy includes a covering that permits PET/CT imaging therethrough and includes CT-visible guides, a plurality of radiation detectors, and wiring connecting the radiation detectors to a power and data control system. During use the garment is wrapped around and secured to the body. The guides are formed from a material that is visible in a computed tomography images. The plurality of radiation detectors are attached to the covering in a configuration customized for the body.

In an embodiment the power and data control system is configured to wirelessly transmit the data from the detectors to a remote service provider.

In an embodiment a plurality of positioning features are incorporated into the covering and operable to facilitate attaching the garment to the body in a repeatable position, for example, the positioning features may be apertures or windows that are configured to overlie corresponding fiducial markers on the body.

In an embodiment the radiation detectors are individually wired to the power and data control system.

In an embodiment the radiation detectors include a container formed from a material that blocks ionizing radiation, for example lead, and the container defines an aperture into the container. A crystal scintillator and a silicon photomultiplier are operably connected and disposed in the container opposite the aperture. For example, the crystal scintillator may be gadolinium aluminum gallium garnet doped with cerium.

In an embodiment the radiation detectors are collimated spectroscopy counters.

In an embodiment the power and data control system includes a power supply, a receiver configured to receive radiation detection signals from the plurality of radiation detectors, and a transmitter configured to transmit the received signals.

In an embodiment the plurality of detectors are disposed in a sparse array.

A method for detecting radiation emitted from one or more organs in a body undergoing internal radionuclide therapy, and transmitting signals characterizing the detected radiation, includes (i) providing a garment configured to be secured around the body during positron emission tomography-computed tomography (PET/CT) and to permit imaging a portion of the body through the garment, wherein the garment further comprises grid markings that are configured to be visible in computed tomography images through the garment, (ii) marking the body with a plurality of fiducial markers; (iii) attaching the garment to the body in a repeatable position using the fiducial markers; (iv) imaging the body with the garment in the repeatable position using a PET/CT scanner to generate images showing the organs and the grid markings; (v) fixing a plurality of radiation detectors to the garment in locations based on the image obtained from the PET/CT scanner, wherein the detectors are positioned to detect radiation emitted from the organ, wherein the detectors are operatively connectable to the computer and configured to transmit signals characterizing the radiation detected by the detectors to the computer; and attaching the garment to the body in the repeatable position after the body has been injected with a radionuclide and transmitting signals corresponding to the radiation detected by the detectors to the computer.

In an embodiment the step of attaching the garment to the body is performed at least three days after the body has been injected with a radionuclide.

In an embodiment the garment further includes a transmitter operatively connected to the plurality of detectors and configured to wirelessly transmit the signals corresponding to the radiation detected by the detectors to the computer.

In an embodiment the one or more organs is a kidney.

In an embodiment the garment is a belt or a vest.

A wearable dosimetry device for detecting radiation emitted from an organ in a body includes a flexible support that wraps around a body, a guide on the flexible support that is visible in computed tomography images of the device, a plurality of radiation detectors fixed to the flexible support, a processor fixed to the flexible support and in signal communication with the detectors, a wireless transmitter configured to receive data from the processor and to transmit the received data to a receiver, and an electrical power supply configured to provide electrical power to the plurality of detectors, to the processor, and to the wireless transmitter.

In an embodiment the flexible support further comprises a plurality of windows configured to aide in precise positioning of the wearable device to the organ.

In an embodiment the plurality of detectors are arranged in a sparse array on the flexible support.

In an embodiment the plurality of detectors each include a lead container having a first face defining an aperture configured to face the body, and providing access to an interior of the container, and an assembly comprising a scintillator crystal and a photomultiplier disposed on a wall opposite the aperture.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

A known challenge in unsealed source radiotherapy is monitoring the radioactive dose of organs and/or tumors, which requires patients to return multiple times to the medical service provider for longitudinal imaging to determine organ dosimetry. Organ dosimetry provides a basis for determining the amount of additional therapeutic dose that a patient can receive. Some radiotherapies, for example, peptide receptor radionuclide therapy (PRRT), are approved for every patient receiving the same standard dosing (e.g., for $^{177}$Lu-DOTATATE, four treatment doses of 200 mCi each). Studies have shown, however, that for some patients the approved dosing will deliver an unsafe dose to the patient's organs, and for other patients more than four treatment doses may be safely used before organ toxicity is a problem. Monitoring the washout of radionuclides (e.g., the organ radioactivity concentrations) in a patient would allow the actual dosing for organs at risk (OARs) and for tumors, to be calculated. Determining (or estimating) the actual dosing would allow an optimal treatment plan to be personalized to the individual patient. For example, some treatment protocols for PRRT require patients to undergo 3-4 imaging sessions after receiving the radionuclide for each treatment, for example, at 24 hours, 72 hours, and 168 hours from the injection of the radionuclide, to obtain organ dosimetry measurements. Multiple visits to a medical facility can be expensive and burdensome to the patient and to the medical facility.

A personalized dosimetry garment is disclosed that is configured to measure and report radioactive emissions from user organ, tumor, and/or other regions of interest. The garment may be used at home, obviating the need for at least some longitudinal clinic visits. For example, in some embodiments a quantitative SPECT/CT scan is performed at the clinic shortly after injecting the radiopharmaceutical (e.g., approximately 24 hours after dose administration), but additional clinical imaging (for example, at 4 and 7 days after injection) are not obtained. Rather, subsequent dosimetry data is obtained from the personalized garment. The garment may include, for example, 6-15 small radiation detectors placed at locations that are determined based on the user's anatomy. The garment wraps around the user, for example, in the form of a belt, vest, or other wrap. Including detectors and electronics, the garment may be relatively light weight, for example, weighing less than 750 grams (1.65 pounds).

The garment allows radiation washout measurements (organ radioactivity concentrations) to be taken over many days at the user's home, and allows for more frequent monitoring. For example, measurements may be obtained daily. For PRRT applications, for example, daily measurements for between 7 to 21 days would allow for more accurate estimation of $^{177}$Lu-DOTATATE dosimetry from the kidneys than current procedures, for example, taking three or four nuclear medicine clinical images spaced days apart. The garment requires only a few minutes to position on the user. In some embodiments an entire measurement and reporting procedure may require less than six minutes to complete. The garment in a currently preferred embodiment includes battery operated electronics for data acquisition (e.g., detectors and related amplifier electronics), storage, and transmission. For example, the garment may include wireless communication capabilities, configured to send encrypted data to a secure website. The garment may further provide feedback to allow medical staff to remotely monitor if the user is wearing the device and using it properly. Therefore, the medical staff may contact the user to address issues if problems occur. A further advantage of daily monitoring is that the loss of 1 or 2 recordings will not significantly reduce accuracy of the organ (e.g., kidney) dosimetry estimates. The garment disclosed herein may be produced relatively inexpensively making it very feasible as a piece of home-use durable medical equipment. While the garment is customized for each user, the individual components, for example, the radiation detectors and electronics may be reusable.

A method and system is disclosed that allows more frequent measurements to be taken, optionally over a longer period of time, to better characterize the washout of the radiotracer from organs and/or tumors of interest, while greatly reducing the costs and burden to the user, by permitting users to obtain organ and/or tumor radiation data from home, at more frequent intervals, and to transmit the data to the service provider.

Figure 1A:
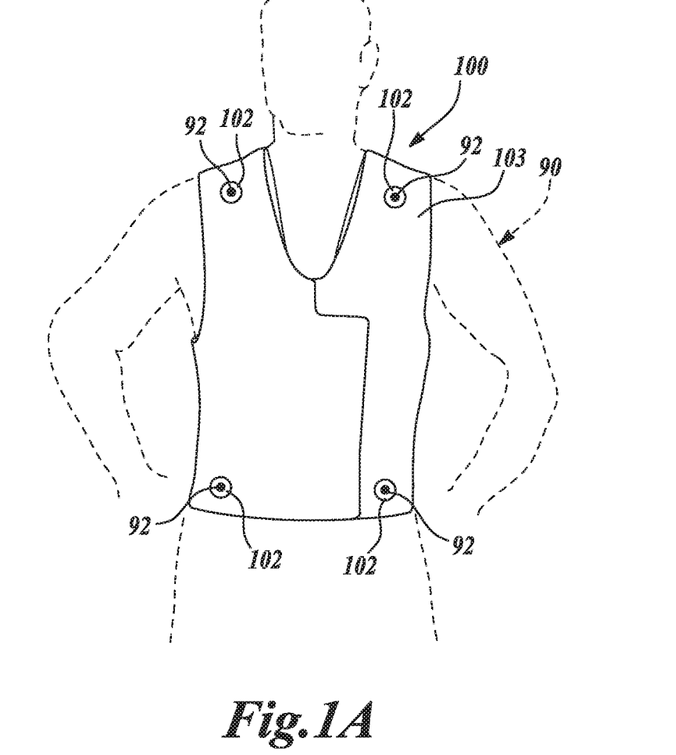
FIG. 1A shows a garment, in this embodiment a vest, in accordance with the present invention, shown in the worn configuration.
Figure 1B:
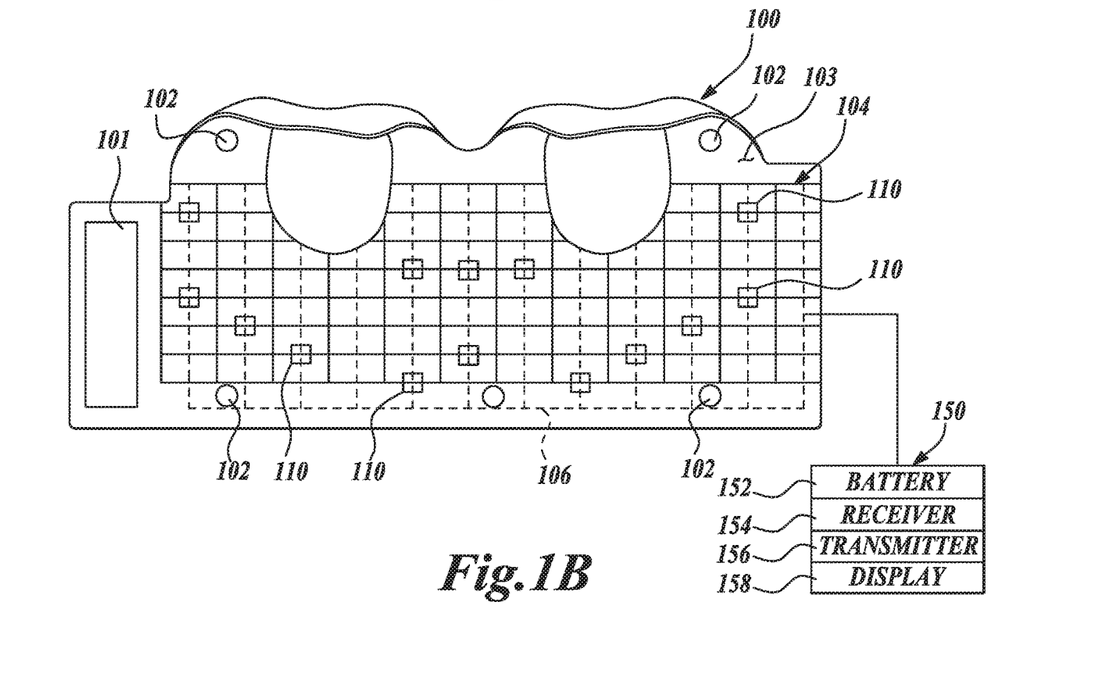
FIG. 1B is the garment shown in FIG. 1A, shown in an open configuration.

A garment 100 in accordance with the present invention is shown in FIGS. 1A and 1B. In this embodiment the garment 100 is a vest. The garment 100 is illustrated in a worn configuration in FIG. 1A, and in an open configuration in FIG. 1B. The garment 100 is operable to detect radiation emitted from organs and/or tumors in the wearer of the garment 100. The disclosed system is configured to measure or estimate the washout of radioactivity from the organs (organs at risk) and/or tumors. It is contemplated that a garment in accordance with the present invention may be configured to measure radiation in any targeted region of interest in the wearer.

The garment 100 includes a flexible substrate or covering 103 that engages the user 90 securely such that the garment 100 will resist or avoid shifting relative to the user 90 during use, for example, with a closure mechanism 101 for securing the garment 100 to the user 90, for example, hook and loops fastener, belts and clasps, or other fastening means as are known in the art. The covering 103 may be customized to the user, or may be produced in a number of standard sizes, with a suitable size selected and optionally adapted to the particular user.

A plurality of radiation detectors 110 are supported by the covering 103, oriented inwardly in selectable locations. In the current embodiment the plurality of detectors 110 are arranged in a sparse array wherein the locations of the detectors 110 are customized to the user's 90 anatomy, in particular considering the location of the user's organs, and the location of any tumors of interest. A wiring system 106 connects the radiation detectors 110 to a power and data control system 150 that may be partially or fully integrated into the garment 100 or separate from the garment 100. For example, in a currently preferred embodiment the radiation detectors 110 are individually wired to the control system 150. Alternatively, a wiring network may be incorporated into the garment 100. Other wiring options are known and will be obvious to persons of skill in the art. Although in the current embodiment the garment 100 is configured to support radiation detectors 110 at locations substantially anywhere on the garment 100, in some applications the garment may be configured to support detectors 110 over a more limited region of the garment.

One or more components of the system 150 may be separate from the garment 100. It is contemplated that the garment 100 may be made in separable parts. For example, the garment 100 may include an outer covering 103 that defines a recess on an interior side, and an inner portion, for example, a circuit board assembly that incorporates the detectors 110 and is supported in the covering recess. In other embodiments the garment 100 may include an array of ports or recesses on an interior surface that are configured to selectively receive and retain the radiation detectors 110.

The garment 100 includes a mechanism to facilitate positioning the garment 100 to the user 90 accurately and reproducibly at a desired location on the user 90. For example, a plurality of fiducial markers 92 may be applied to the user (e.g., temporary tattoos) in desired locations to provide guides for positioning the vest 100. In this embodiment the garment 100 includes a plurality of apertures or windows 102. The fiducial markers 92 are configured to align with the windows 102 and to be visible therethrough when the garment 100 is in the desired position on the user 90. In this embodiment, the user dons the garment 100, aligns the windows 102 with the fiducial markers 92, and secures the garment 100 with the closure mechanism 101.

The garment 100 further includes radiopaque markings or guides 104, e.g., a CT-visible grid. The guides 104 are configured to be visible in CT images. Preferably, the guides 104 are substantially transparent to photons having energy greater than 70 keV. The guides 104 are therefore visible in CT images of the user 90 wearing the garment 100 (e.g., with the garment 100 worn in the desired, repeatable or reproducible position), such that the guides 104 are visible in images of the user's 90 organs in PET/CT images of the user 90 wearing the garment 100. These images are used to register the location of the user's organs (e.g., OARs) with the garment 100 such that an optimal number and location for the detectors 110 may be determined for installation of the detectors 110. In many applications the imaging with the guides 104 for registering the organs will not require a separate image scan. For example, typically when preparing for $^{177}$Lu-DOTATATE therapy the patient first receives a $^{68}$Ga-Dotatate PET/CT (positron emission tomography/computed tomography) scan to ensure the tumors are SSTR2 positive. The garment 100 may be worn during this pretreatment imaging scan (without the detectors 110), and these images may be used to register the user's organs with the garment 100.

The radiation detectors 110 are operatively connected to the power and data control system 150, for example, through direct wiring 106. The system 150 in this embodiment includes a power source 152, for example, batteries configured to provide power to the detectors 110 and other components, a receiver and/or processor 154 operably connected to receive data from the plurality of detectors 110, and a transmitter 156 configured to transmit the received data, for example, wirelessly and/or through phone lines (not shown). Optionally, a display 158 is provided that may include various indicators. For example, indicators may be provided to (i) indicate if the garment 100 is properly positioned on the user, (ii) indicate when data is being received, (iii) indicate an elapsed time or remaining time for obtaining data, (iv) indicate when data is being transmitted, or (v) indicate when data has been received and verified by a remote receiver, etc.

Figure 2A:
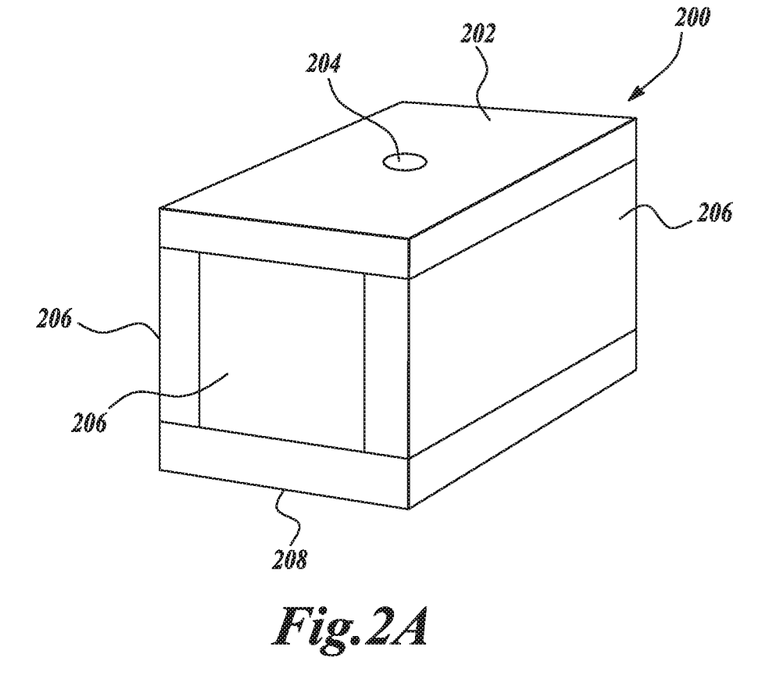
FIG. 2A illustrates one of the radiation detectors for the garment shown in FIGS. 1A and 1B.

In a current embodiment the radiation detector 200 is a crystal scintillation detector. An example of the radiation detector 200 is shown in FIG. 2A and in cross section in FIG. 2B. The detector 200 includes a small enclosure, for example, a lead enclosure formed from side walls 206, a front wall 202 having an aperture 204, and a wall 208 opposite the front wall 202. For example, in one embodiment the aperture 204 may be a 0.3 cm in diameter. In other embodiments the aperture may be smaller or larger, for example, between 0.5 mm and 0.6 cm. A crystal scintillator 210, for example, gadolinium aluminum gallium garnet doped with cerium (GAGG(Ce)), is disposed in the container with a silicon photomultiplier (SiPM) 212 and disposed opposite the aperture 204. It will be appreciated by persons of skill in the art that the detectors 200 in this embodiment functions as collimated, miniature, spectroscopy counters. In some embodiments the orientation of the detector 200 may be adjustable, for example, to control and optimize the orientation of the apertures 204 in the detectors 200. In some embodiments the radiation detectors have capability beyond energy discriminating and counting capabilities, for example, imaging capabilities, e.g., photon position sensing capability to determine photon interaction positions. Other types of radiation detectors are contemplated, as are known in the art, for example, electronic personal dosimeters, such as PIN dosimeters, MOSFET dosimeters, and the like. The photon-positioning capability of the detectors 200 provides additional advantages for the garment 100. For example, photon position information may be used to determine or confirm the position of the garment 100 with respect to the user's organs, for example, to aid in interpreting the data received from the detectors 200 (e.g., such that the received data may be properly interpreted, even if the garment is not accurately positioned) and/or to determine and alert the user if the garment 100 is not properly positioned.

Figure 2B:
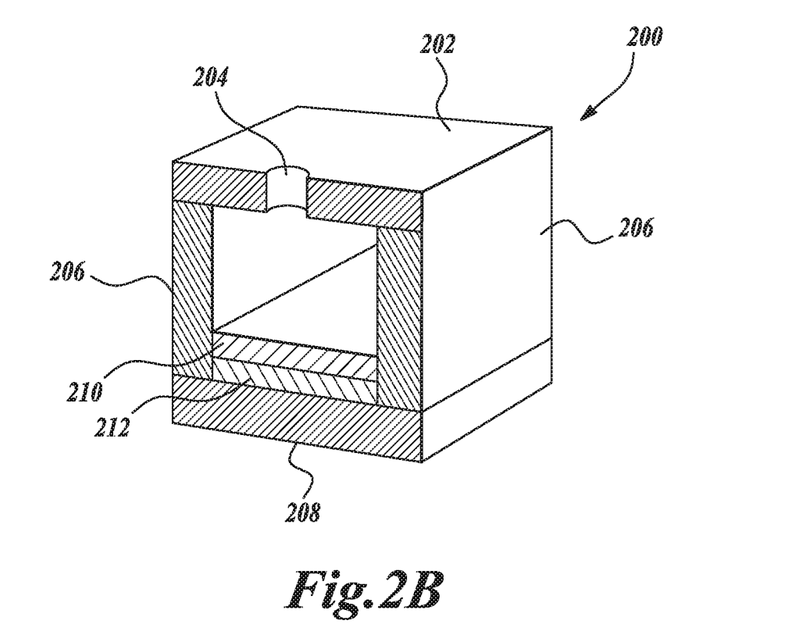
FIG. 2B is a sectional view of the radiation detector shown in FIG. 2A.

Although the currently preferred embodiment includes a customized, sparse array of radiation detectors 200, in other embodiments a garment in accordance with the present disclosure may include a dense array of detectors 200, for example, a rectangular array of detectors 200. However, the sparse array of detectors 200 with placement customized for the user, provides many advantages, including reduced weight, cost, and complexity.

Figure 3:
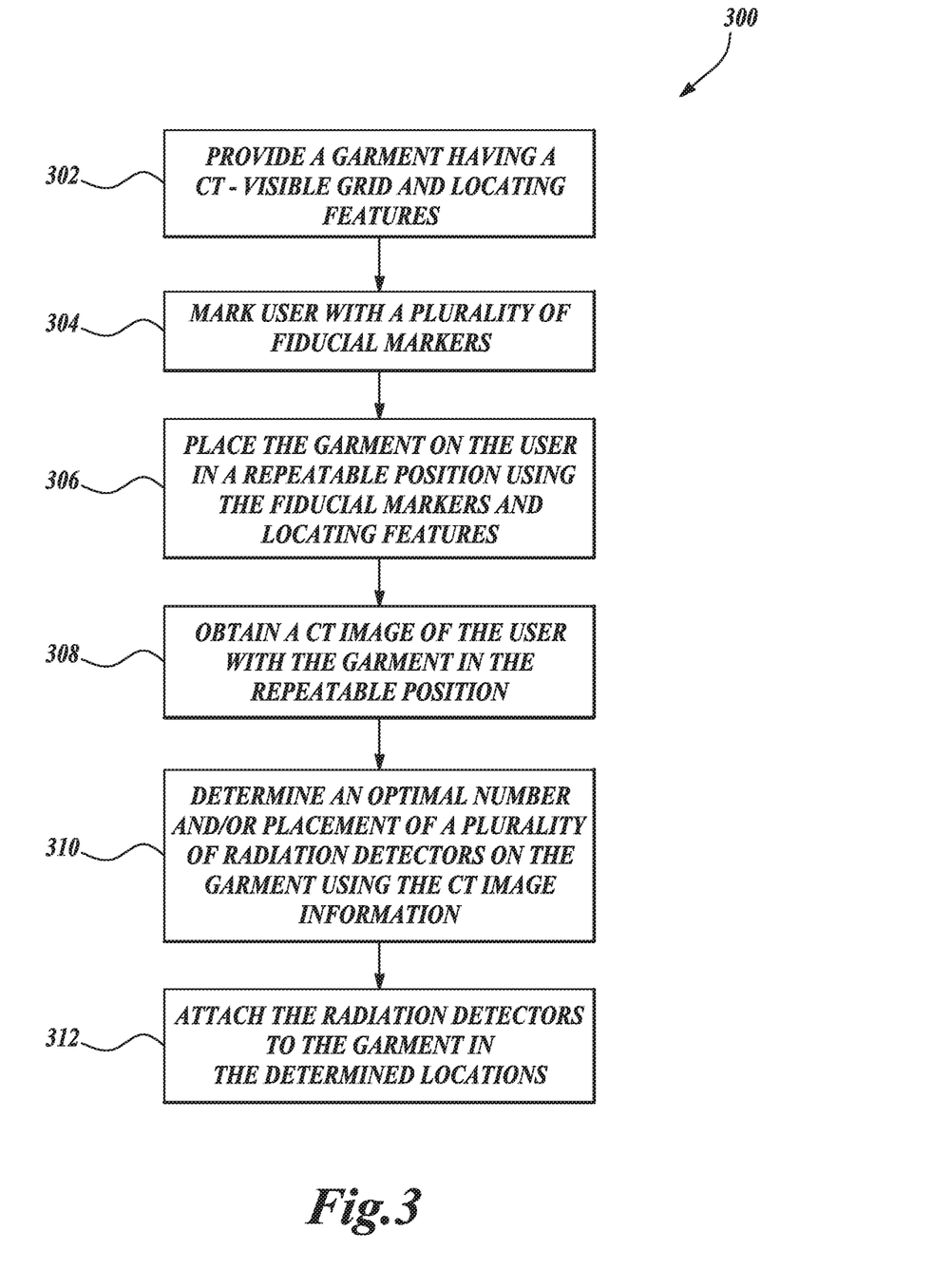
FIG. 3 is a flow chart illustrating a method of providing a customized garment for obtaining radiation washout data in accordance with the present invention.

Refer now to FIG. 3, which presents an example of a method 300 of providing a customized garment 100 for obtaining radiation washout data for organs and/or tumors. The method includes providing a garment 100, for example, a vest, belt, or wrap, having a CT-visible grid and locating features 302, wherein at least a portion of the garment is transparent to high energy photons. In a current embodiment, the user is marked with a plurality of fiducial markers 304 that are configured to cooperate with the garment to facilitate placing the garment on the user at a desired and repeatable position. The garment is placed on the user in the repeatable position 306 using the fiducial markers. It is contemplated by the present invention that other methods may be used to position the garment on the user in a repeatable position, for example, providing a rigid outer shell that is customized to the user.

With the garment in place, a CT image of the user is obtained 308 with the grid visible in the images, allowing the user's organs (visible in the CT or PET/CT image) to be registered to the garment grid. A customized optimal number and placement of radiation detectors for the garment is then determined 310. For example, in a current method simulation studies using Monte Carlo simulations are performed to optimize the detector placement based on the user-specific anatomy. Monte Carlo simulations are well known in within the skill in the art. The radiation detectors are then attached to the garment and configured to detect radiation from at least one organ (or tumor) of the user 312.

Figure 4:
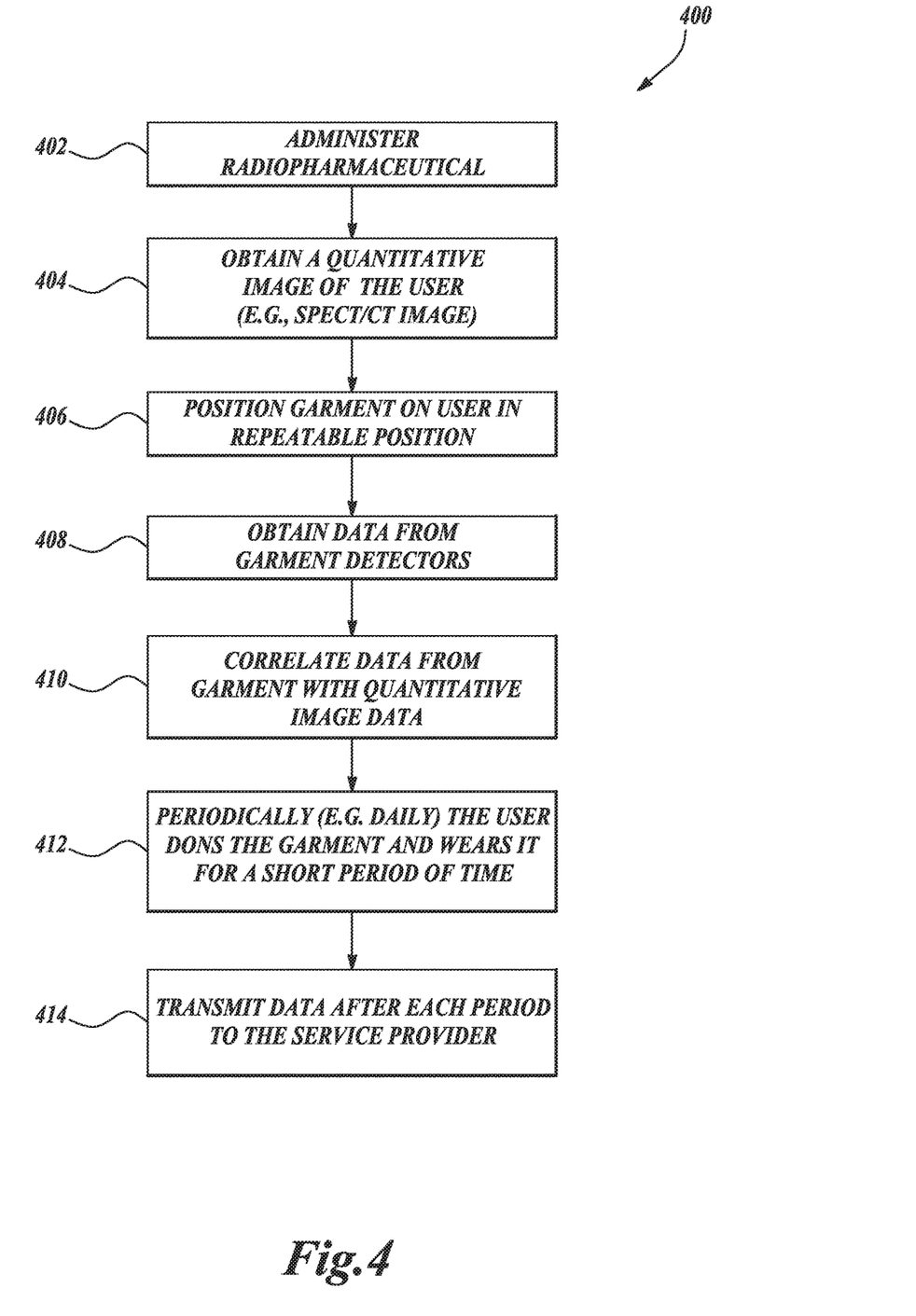
FIG. 4 is a flow chart illustrating a method for using the garment shown in FIG. 1A.

FIG. 4 presents an example of a method 400 for obtaining washout data for organs and/or tumors using the garment 100 in accordance with the present invention. In this embodiment the radiopharmaceutical is administered to the user 402, for example, by injection or orally. A quantitative image of the user, for example a SPECT/CT image, is obtained shortly after the radiopharmaceutical is administered 404 (e.g., 24 hours after administration). Immediately or shortly after the quantitative imaging, the garment 100 is positioned on the user in the repeatable position 406. Dosimetry information, i.e., detected radiation data is obtained from the garment 408, as discussed above. Data from the radiation detectors in the garment are correlated with the quantitative image results 410.

In subsequent days the user periodically (e.g., daily) dons the garment in the repeatable position 412. For example, in the present invention this step may be done at the user's home. The user wears the garment in the repeatable position for a relatively short period of time, for example two to five minutes. Data from the plurality of detectors 110 in the garment 100 are transmitted to the medical service provider after each period 114. For example, the data may be transmitted directly from the power and data control system 150, for example, via WI-FI® or through a cellular network.

It will be appreciated by persons of skill in the art that the disclosure and teachings herein may be applied to other procedures and therapies. In particular, a customized, monitoring and data transmitting garment in accordance with the present disclosure may be applied to any method or treatment that requires obtaining localized radiation emission estimates from internal locations in a body.

For example, another contemplated application is proton beam therapy dose and position monitoring. In this application the garment may be a circular hoop around a patient. During proton therapy for cancer treatment, a beam of protons is directed to the region in the patient containing the tumor. The protons "pile up" in the Bragg peak (a peak on the Bragg curve plotting the energy loss of ionizing radiation during travel through matter), allowing for localization of the protons by positioning the Bragg peak at the tumor position. In proton beam therapy the protons are specifically directed to cells within the Bragg peak, and therefore spares much of the healthy tissue along the path of the beam. This is opposed to the external beam radiotherapy that utilizes high-energy photons, where all tissue in the path of the beam, including healthy tissue, is irradiated and subject to damage.

Determining the trajectory of the proton beam and the location of the Bragg peak is a non-trivial task. During proton beam therapy it is useful to have real-time tracking of the position of the Bragg peak. If the position of the Bragg peak is not accurately determined, the proton therapy can damage healthy tissue and leave a tumor untreated.

During proton therapy, some of the proton interactions generate positrons that can be imaged using the techniques of positron emission tomography (PET). There have been attempts to use PET for Bragg peak localization, with some success. However, PET systems are expensive and generally require a full ring of sensors to generate an image.

Adapting the teachings described above, a patient wears a garment (e.g., in a ring or cylinder geometry) with custom positioned detectors. The detector positions in the garment are optimized to image positrons for estimating the location of the Bragg peak in the patient's body using PET methodologies. In this configuration, the output from the vest is a real-time image or indicator of the position of the Bragg peak. This image can be superimposed on a CT scan of the patient for real-time tracking and positioning of the proton beam Bragg Peak. In this application the garment itself may be standardized for different patients, but the detectors positions are customized to the user, to provide optimal detection during the proton beam therapy.

In another example, a garment in accordance with the present invention may be used to perform dynamic PET (Dynamic PET) imaging. In conventional (static) PET imaging, a patient is injected with a radiotracer and placed in the PET scanner for imaging, typically approximately an hour after the radiotracer injection, to image the regions where the radiotracer has accumulated.

In Dynamic PET imaging the user is injected with the radiotracer while within the scanner, allowing the scanner to visualize the change in radiotracer concentration over time. A common goal for Dynamic PET imaging is to draw a region of interest (ROI) around a tumor and monitor how the concentration of radiotracer changes over time. This gives additional information of the tumor metabolism that is generally not available with the standard static PET imaging. However Dynamic PET requires additional workforce in the clinic, determination of an input function (i.e., blood activity concentration over time), more time on the scanner, produces much noisier images than static PET, and is significantly more expensive than static PET. For these reasons, Dynamic PET is not used regularly.

Applying the teachings described above, a garment having a plurality of radiation detectors that are positioned in the garment based on the user's anatomy, wherein the CT scan of the patient is analyzed to determine the optimal detector locations to facilitate Dynamic PET. The user wears the customized garment during injection of the radiotracer. The detectors in the garment are positioned to estimate the blood activity input function and to monitor the radiotracer concentration within the region of interest defined by the physician. The output from the garment in this application is used to produce an "input function" and a "time-activity curve" common in dynamic imaging. This embodiment is not limited to PET imaging, but may also be applied to Dynamic SPECT (Single Photon Emission Computed Tomography) imaging methods, for example.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for detecting radiation emitted from one or more organs in a body undergoing internal radionuclide therapy, and transmitting signals characterizing the detected radiation, comprising:
   providing a garment configured to be secured around the body during positron emission tomography-computed tomography (PET/CT) and to permit imaging a portion of the body through the garment, wherein the garment further comprises grid markings that are configured to be visible in computed tomography images through the garment;
   marking the body with a plurality of fiducial markers;
   attaching the garment to the body in a repeatable position using the plurality of fiducial markers;
   imaging the body with the garment in the repeatable position using a PET/CT scanner to generate images showing the one or more organs and the grid markings;
   fixing a plurality of radiation detectors to the garment in locations based on the images obtained from the PET/CT scanner, wherein the detectors are positioned to detect radiation emitted from the one or more organs, wherein the detectors are operatively connectable to a computer and configured to transmit signals characterizing the radiation detected by the detectors to the computer;
   removing the garment from the body;
   injecting the body with a radionuclide;

attaching the garment to the body in the repeatable position after the body has been injected with the radionuclide; and transmitting signals corresponding to the radiation detected by the detectors to the computer.

2. The method of claim 1, further comprising: after the body has been injected with the radionuclide, periodically attaching the garment to the body.

3. The method of claim 1, wherein the garment further comprises a transmitter operatively connected to the plurality of detectors and configured to wirelessly transmit the signals corresponding to the radiation detected by the detectors to the computer.

4. The method of claim 1, wherein the one or more organs comprises a kidney.

5. The method of claim 1, wherein the garment comprises a belt or a vest.

* * * * *